United States Patent [19] [11] Patent Number: 5,049,128
Duquette [45] Date of Patent: Sep. 17, 1991

[54] VALVED INFUSION PORT

[76] Inventor: Irene A. Duquette, 172 Punkup Rd., Oxford, Conn. 06483

[21] Appl. No.: 475,737

[22] Filed: Feb. 6, 1990

[51] Int. Cl.⁵ ............................................. A61M 37/00
[52] U.S. Cl. ...................................... 604/83; 604/249
[58] Field of Search .................. 604/284, 83, 86, 249, 604/256, 246

[56] References Cited

U.S. PATENT DOCUMENTS

| 2,999,499 | 9/1961 | Willet | 604/83 |
| 3,416,567 | 12/1968 | Von Dardel et al. | 604/83 |
| 3,994,293 | 11/1976 | Ferro | 604/83 |
| 4,121,585 | 10/1978 | Becker, jr. | 604/86 |
| 4,333,455 | 6/1982 | Bodicky | 128/214.4 |
| 4,585,435 | 4/1986 | Vaillancourt | 604/27 |
| 4,596,557 | 6/1986 | Pexa | 604/86 |
| 4,661,110 | 4/1987 | Forter et al. | 604/284 |
| 4,752,287 | 6/1988 | Kurtz et al. | 604/99 |
| 4,816,020 | 3/1989 | Brownell | 604/97 |
| 4,915,687 | 4/1990 | Sivert | 604/249 |

Primary Examiner—Stephen C. Pellegrino
Assistant Examiner—Ralph A. Lewis
Attorney, Agent, or Firm—Ailes, Ohlandt & Greeley

[57] ABSTRACT

A valved infusion port of an infusion system comprising an injection unit having a primary infusion port and at least one secondary infusion port, characterized by the improvement to the secondary infusion port comprising: a bidirectional valve means disposed about the secondary infusion port; whereby the bidirectional valve means is capable of opening and closing the secondary infusion port to permit the administration of a secondary infusion without the use of a needle.

8 Claims, 3 Drawing Sheets

VALVED INFUSION PORT

The present invention relates primarily to modification of a secondary infusion port of an infusion system to include a two-way spring valve assembly which permits access to the primary infusion by a secondary infusion via a syringe or secondary tubing without the use of a needle. This novel device completely eliminates the possibility of infections, e.g., hepatitis B or AIDS, resulting from needle sticks caused by use of infusion systems requiring needles for accessing the primary infusion with a secondary infusion.

BACKGROUND OF THE INVENTION

The current practice necessitates the use of a needle through a self sealing rubber stoppered port in a Y-shaped injection unit. Some examples demonstrating the use of needles at a Y-shaped injection unit are U.S. Pat. Nos. 4,121,585 (Becker, Jr.), issued Oct. 24, 1978, 4,585,435 (Vaillancourt), issued Apr. 29, 1986, and 4,596,557 (Pexa), issued June 24, 1986.

The health risk associated with needle sticks has become of great concern to the medical community. This is evidenced by the recently published article, "Despite Safety Guidelines, Various Devices Still Cause Needle-Stick Injuries," *Oncology Nurse Bulletin,* (NCM Publishers, Inc.), October 1988, pp. 2 and 8. This article discusses the complacency about needle sticks which causes approximately 300 health care workers to die each year from direct or indirect consequences of occupational acquired hepatitis B, not to mention the number which test positive each year to AIDS testing. The article continues to state that "the second most common cause of needle sticks, and the biggest rate of injury, came from accidents involving intravenous tubing needle assemblies". In these accidents, over one quarter were related to recapping, and this was probably due to the fact that the needle caps were unavailable when intravenous lines were dismantled. The needle sticks occurred when alternative methods, such as introducing needles into drip chambers, intravenous ports or bags, were used for covering the needles.

Thus, needle sticks can occur from recapping of needles, poor needle connections, attempts at removal of a needle by loosening of the needle hub from the tubing, and when the needle is either manually or accidental dislodged from the tubing.

Any injury from a used needle is potential for infection, especially hepatitis B and AIDS. FIG. 2, attached hereto, depicts a conventional infusion port 50 which includes a polyvinylchloride primary infusion tubing 51, tubing 56, Y-shaped injection unit 52, and self sealing rubber stopper 54. Y-shaped injection unit 52 includes a primary infusion port 58 and a secondary infusion port 59. During administration of a secondary medication or other fluid a needle 55 is injected into self sealing rubber stopper 54 located about the opening of secondary infusion port 59. After injection needle 55 is capable of introducing a secondary infusion into Y-shaped injection unit 52.

Needle sticks occur during the injection and withdrawal of needle 55 from stopper 54, and at most anytime when the needle is uncapped, transported or disposed. Since intravenous injections are common place in medical treatment, it is entirely to risky to continue to expose medical personnel to needle sticks which can lead to the contraction of infectious diseases.

The present inventor has developed a unique device which does not require the use of needles to deliver secondary medications to intravenous systems, thereby completely eliminating the threat of contracting infectious diseases when a secondary medication or blood transfusion is administered via an intravenous system.

One device which attempts to eliminate the use of needles during the administration of secondary medications or blood transfusions to the Y-shaped injection unit of an intravenous system is set forth in U.S. Pat. No. 3,994,293 (Ferro), issued Nov. 30, 1,976. The Ferro patent describes an injection assembly which can be used in combination with a feeding means (e.g., a syringe) for feeding, into a transfusional or perfusional liquid, a nourishing solution, a vitamin solution, a medicinal solution, an anticoagulant solution or a like solution, wherein penetration of a hollow piercing member (e.g., a syringe needle) into the injector body is not necessary. The purpose of the device set forth in the Ferro patent is to overcome the disadvantages caused by repeatedly injecting new needles into the injector wall. That is, after repeated injections the injector wall weakens and is no longer adequately sealed.

The Ferro patent makes use of a liquid pressure-actuated elastomeric diaphragm positioned in the tubular branch portion. The diaphragm includes a pre-perforated portion formed having a pressure threshold corresponding to a predetermined pressure of the solution upstream of the diaphragm. The pre-perforated portion is normally impervious to prevent passage of the solution through the tubular branch portion of the tubular conduit portion when the pressure of the solution upstream of the diaphragm is less than the pressure threshold. The pre-perforated portion becomes pervious to allow passage of the solution through the tubular branch portion to the tubular conduit portion when the pressure of the solution upstream of the diaphragm is at least equal to or greater than the pressure threshold. Furthermore, a valve means cooperating with the pre-perforated portion of the diaphragm only permits unidirectional feeding of the solution in the tubular portion through the pre-perforated portion to the tubular conduit portion, but not vice versa.

One disadvantage of the injector assembly set forth in the Ferro patent is that it causes air in the tubing and does not permit bidirectional movement of the pre-perforated portion of the diaphragm.

Various needleless syringe assemblies have been designed for use in catheter devices, e.g., U.S. Pat. Nos. 4,752,287 (Kurtz et al.), issued June 21, 1988, 4,816,020 (Brownell), issued Mar. 28, 1989, and 4,333,455 (Bodicky), issued June 8, 1982. These devices are concerned with inflation of catheter balloons and not the injection of secondary medicines or solutions into an intravenous system.

The present invention overcomes the aforementioned disadvantages of conventional intravenous injection systems by providing a device which eliminates the use of needles in the administration of secondary medications or other solutions via a Y-shaped injection port. The present invention also completely eliminates the risk of contracting an infectious disease due to needle sticks during the handling of intravenous systems.

The present invention accomplishes the aforementioned advantages by providing a novel two-way valve infusion port which permits administration of secondary medications or other solutions without the injection of a needle and permits bidirectional movement of the valve to avoid backflow of solution or air contamination of the intravenous system.

Additional advantages of the present invention shall become apparent as described below.

SUMMARY OF THE INVENTION

A valved infusion port of an infusion system comprising an injection unit having a primary infusion port and at least one secondary infusion port, characterized by the improvement to the secondary infusion port comprising: a bidirectional valve means disposed about the secondary infusion port; whereby the bidirectional valve means is capable of opening and closing the secondary infusion port to permit the administration of a secondary infusion without the use of a needle.

The bidirectional valve means is a two-way spring valve which allows a secondary infusion to flow freely through the secondary infusion port to the injection unit and upon removal of the syringe or secondary tubing the two-way spring valve closes to keep air out of the infusion system and prevent the primary infusion from leaking out through the secondary infusion port. The two-way spring valve is preferably disposed directly within the walls of the secondary infusion port.

One preferred valve design includes a valve plunger, a spring means, a valve port, sealing means, and conduit means capable of transporting secondary infusion to the injection unit. The spring means is connected to the valve plunger in such a way as to permit the opening and closing of the valve.

An additional object of the present invention is the application of a closing means about the secondary infusion port for keeping it sterile. The closing means is typically a cap or stopper.

The present invention may also include many additional features which shall be further described below.

DESCRIPTION OF THE PREFERRED EMBODIMENTS

A secondary infusion port of an infusion system which includes a two-way spring valve assembly capable of permitting access to the primary infusion by a syringe or secondary tubing without the use of a needle. This valved infusion port completely eliminates the possibility of infections, e.g., hepatitis B or AIDS, resulting from needle sticks caused by use of infusion systems requiring needles for accessing the primary infusion with a secondary medication or other solution.

The present invention provides for the needleless injection of a secondary infusion into a Y-shaped injection unit by attaching a syringe, leur lock tubing or straight intravenous secondary tubing to a bidirectional valve of a secondary infusion port. The valved secondary infusion port also maintains a closed system in the intravenous line, i.e., keeps fluid in and air out.

Figure 1:
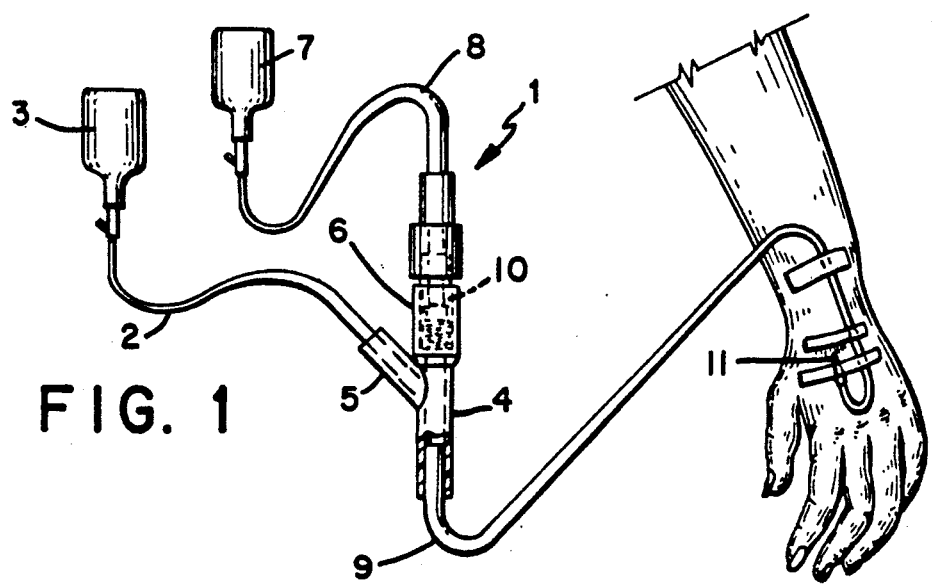
FIG. 1 is a schematic representation of an intravenous system which includes a valved infusion port in accordance with the present invention.
Figure 2:
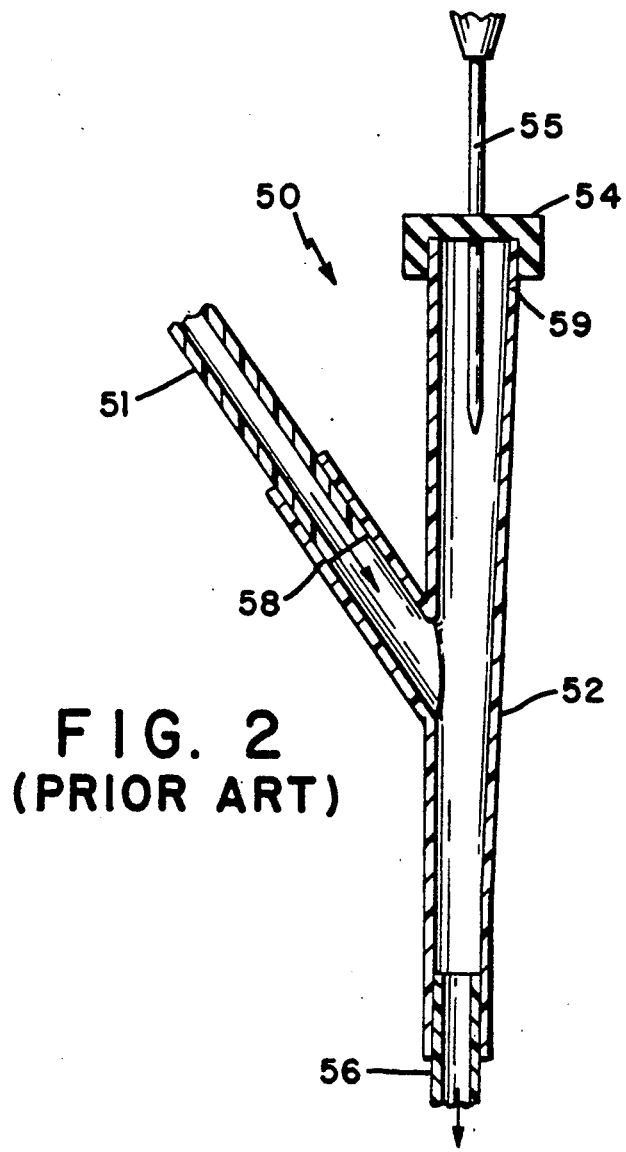
FIG. 2 is a schematic representation of a conventional Y-shaped injection unit having a self sealing rubber stopper at a secondary infusion port.

The present invention can best be described by referring to the attached drawings. FIG. 1 depicts an intravenous system 1 which comprises primary tubing 2, primary solution bottle 3 and Y-shaped injection unit 4. Y-shaped injection unit 4 includes primary infusion port 5 and secondary infusion port 6. Primary tubing 2 is connected to Y-shaped injection unit 4 via primary infusion port 5. Primary tubing 2 is affixed to Y-shaped injection unit 4 at primary infusion port 5 by any suitable means, including, but not limited to, heat sealing.

Secondary infusion port 6 which includes a two-way valve 10 is used to introduce a secondary medication or solution contained in secondary solution bottle 7 into Y-shaped injection unit 4. Use of two-way valve 10 allows the administration of secondary medication or solution from secondary solution bottle 7 without the use of a needle. That is, two-way valve 10 opens to allow the secondary infusion to flow freely through secondary infusion port 6 into Y-shaped injection unit 4, and closes when the secondary infusion means is removed thereby keeping air out and preventing primary infusion administered from primary solution bottle 3 from leaking out through secondary infusion port 6.

By using the valved infusion port of the present invention the danger of needle stick injury to medical personnel during administration and removal of the secondary infusion to an intravenous system is eliminated.

During normal administration of a secondary infusion, primary bottle 3 is lowered to below the base of secondary bottle 7. Secondary bottle 7 empties via gravity flow through secondary tubing 8, Y-shaped injection unit 4, intravenous tubing 9, and needle 11 into the patient. When secondary bottle 7 is empty administration of the primary infusion via primary bottle 3 is resumed without interruption.

Figure 3:
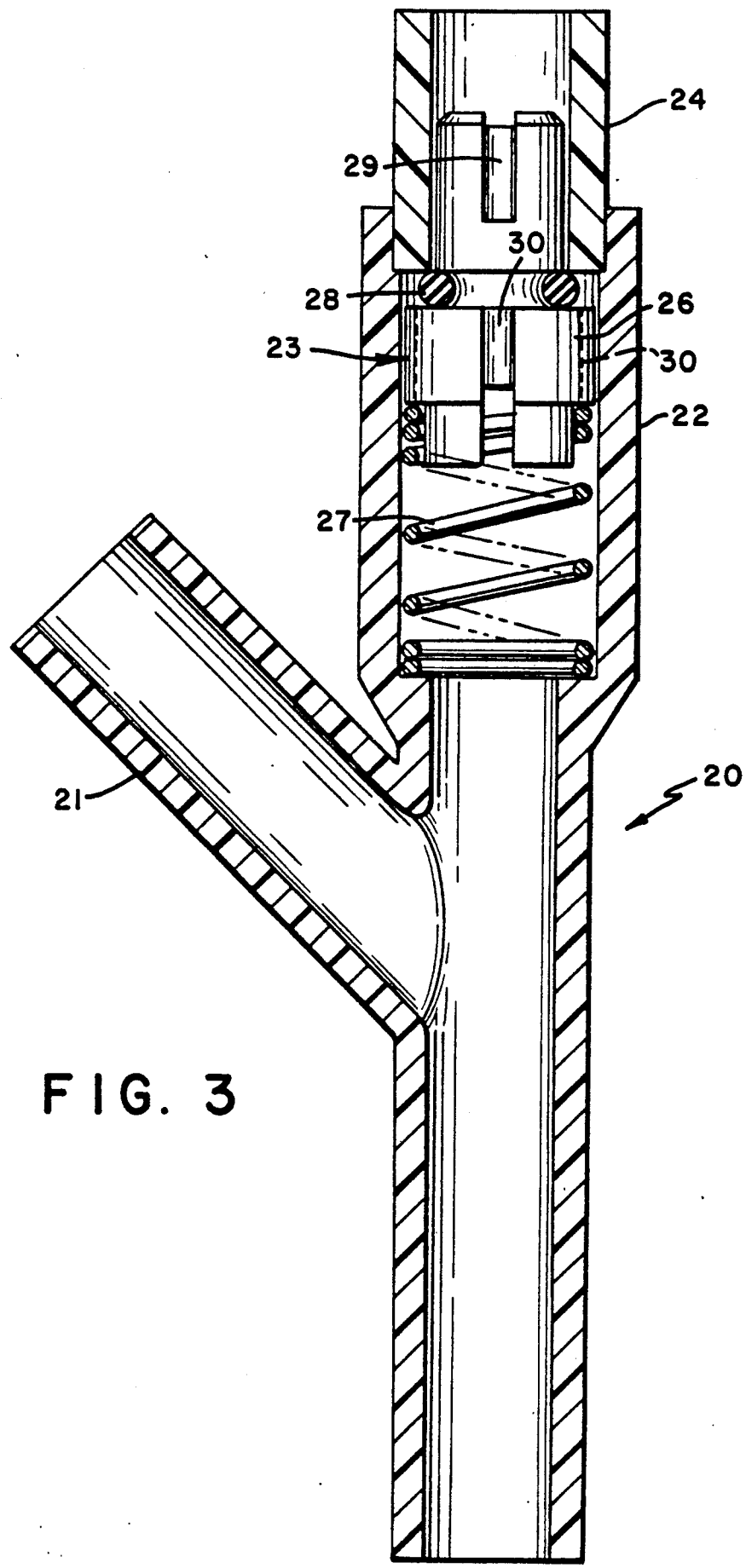
FIG. 3 is a schematic representation of a bidirectional valve disposed within the secondary infusion port of a Y-shaped injection unit in accordance with the present invention.

FIG. 3 depicts a Y-shaped injection unit 20 having a primary infusion port 21 and secondary infusion port 22. Secondary infusion port 22 includes a bidirectional valve means 23. Although bidirectional valve means 23 is depicted as being disposed directly within secondary infusion port 22 it is to be clearly understood that any suitable bidirectional valve means may be used and that the valve may be disposed either within secondary infusion port 22 or simply attached thereto. The unique feature of bidirectional valve means 23 is that it permits access to the primary infusion by a secondary infusion via a syringe or secondary tubing without the use of a needle.

It is preferable that bidirectional valve means 23 be a two-way spring valve which opens to allow a secondary infusion to flow freely through secondary infusion port 22 into Y-shaped injection unit 20 and closes upon removal of a syringe or secondary tubing (secondary infusion means) to keep air out of the infusion system and also to prevent the primary infusion from leaking out through secondary infusion port 22.

A closing means, not shown, is preferably disposed about secondary infusion port 22 and bidirectional valve means 23 for keeping air out of the intravenous system and maintaining sterility. The closing means can be any suitable device, e.g., a plastic flip-top cap or stopper.

FIG. 3 also depicts a preferred two-way spring valve 23 which includes a valve plunger 26, a spring means 27, a valve port 24, sealing means 28, and conduit means (29, 30) which are capable of transporting secondary infusion into Y-shaped injection unit 20.

Spring means 27 is connected to valve plunger 26 in such a way as to permit the opening and closing of conduit means (29, 30). That is, as valve plunger 26 is depressed toward Y-shaped injection unit 20 by a secondary infusion means spring means 27 recoils such that sealing means 28 is no longer in contact with valve port 24, thereby opening conduit means (29, 30) and allowing a secondary infusion to flow from valve port 24 through conduit means (29, 30) into Y-shaped injection unit 20.

Conversely, as the secondary infusion means is removed from valve port 24 spring means 27 expands such that valve plunger 26 moves away from Y-shaped injection unit 20 such that sealing means 28 comes in contact with valve port 24, thereby closing conduit means (29, 30), and preventing air contamination or backflow of primary infusion through secondary infusion port 22.

Spring means 27 is preferably made from surgical grade stainless steel. Sealing means 28 is typically a rubber or plastic 0-ring seal. And the remaining components of valve 23 are preferably made of non-allergic plastics or other suitable materials.

Figure 4:
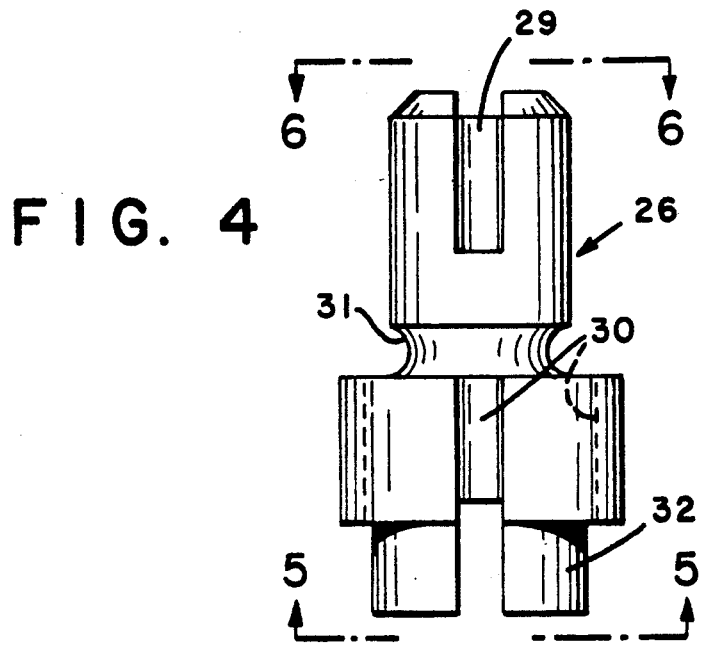
FIG. 4 is a side planar view of the valve plunger depicted in FIG. 3.
Figure 5:
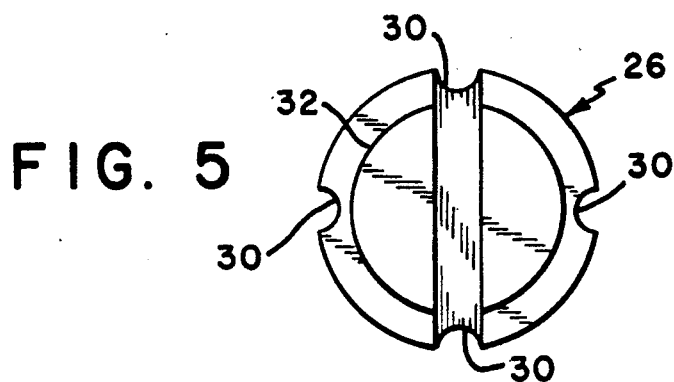
FIG. 5 is a top planar view along line 5—5 of FIG. 4.
Figure 6:
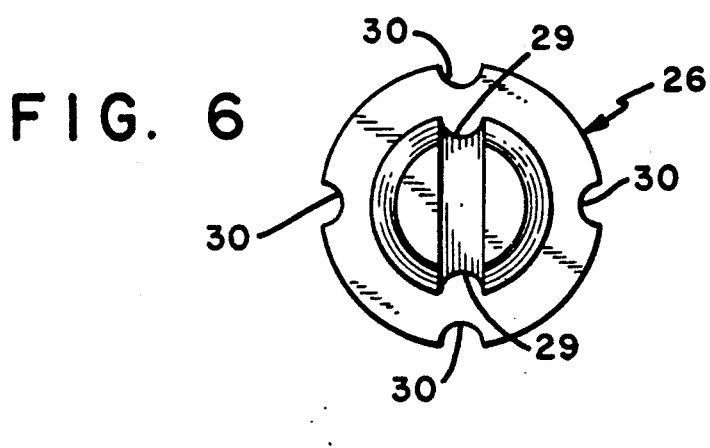
FIG. 6 is a top planar view along line 6—6 of FIG. 4.

FIG. 4 depicts valve plunger 26 having conduit means (29, 30) molded therein. The sealing means, not shown, is disposed about concave portion 31 and spring means, not shown, is attached to valve plunger 26 about portion 32 thereof. FIG. 5 is a top planar view along line 5—5 of FIG. 4 and shows valve plunger 26 with conduit means 30. FIG. 6 is a top planar view along line 6—6 of FIG. 4 and shows valve plunger 26 and conduit means (29, 30).

While I have shown and described several embodiments in accordance with my invention, it is to clearly understood that the same are susceptible to numerous changes and modifications apparent to one skilled in the art. Therefore, I do not wish to be limited to the details shown and described but intend to show all changes and modifications which come within the scope of the appended claims.

What is claimed is:

1. A valved infusion port of an infusion system comprising an injection unit having a primary infusion port and at least one secondary infusion port, characterized by the improvement to said secondary infusion port comprising:

a bidirectional valve means disposed about said secondary infusion port, said bidirectional valve means is a two-way spring valve which comprises: a spring means, a valve port, and a valve plunger having a sealing means a conduit means disposed thereabout, wherein said spring means is connected to said valve plunger in such a way as to permit the opening said conduit means when said spring means is recoiled such that said sealing means is not in contact with said valve port and to permit the closing of said conduit means when said spring means is expanded such that said sealing means is in contact with said valve port; whereby said bidirectional valve means is capable of opening an closing said secondary infusion port to permit the administration of a secondary infusion without the use of a needle.

2. The valved infusion port according to claim 1, wherein a closing means is disposed about said secondary infusion port for keeping said secondary infusion port sterile.

3. The valved infusion port according to claim 2, wherein said closing means is a plastic flip-top cap.

4. The valved infusion port according to claim 2, wherein said closing means is a plastic or rubber stopper.

5. The valved infusion port according to claim 1, wherein said bidirectional valve is connected to either a syringe, a leur lock tubing, or an intravenous tubing.

6. The valved infusion port according to claim 1, wherein said spring means is a stainless steel spring.

7. The valved infusion port according to claim 1, wherein said valve plunger and valve port are formed from plastic or non-allergic plastic.

8. The valved infusion port according to claim 1, wherein said sealing means is a rubber or plastic 0-ring seal.

* * * * *